United States Patent [19]

Sealfon

[11] Patent Number: 5,000,192
[45] Date of Patent: Mar. 19, 1991

[54] PRENATAL SPECIMEN COLLECTION METHOD

[76] Inventor: Andrew I. Sealfon, 713 North St., Middletown, N.Y. 10940

[21] Appl. No.: 459,533

[22] Filed: Jan. 2, 1990

[51] Int. Cl.⁵ .............................................. A61B 5/00
[52] U.S. Cl. ...................................... 128/760; 604/55
[58] Field of Search .............. 128/760, 763, 765, 770; 604/28, 35, 49, 51, 54, 55, 128, 187, 190, 264, 319, 406

[56] References Cited

U.S. PATENT DOCUMENTS

| | | | |
|---|---|---|---|
| 3,224,434 | 12/1965 | Molomut et al. | 128/760 |
| 4,100,923 | 7/1978 | Southern | 604/55 |
| 4,194,513 | 3/1980 | Rhine et al. | 128/750 |
| 4,280,508 | 7/1981 | Barrada | 128/760 |
| 4,308,875 | 1/1982 | Young | 128/753 |
| 4,366,822 | 1/1983 | Altshuler | 128/765 |
| 4,681,123 | 7/1987 | Valtcher | 128/753 |
| 4,685,472 | 8/1987 | Muto | 128/760 |
| 4,697,600 | 10/1987 | Cardenas et al. | 128/753 |
| 4,729,764 | 3/1988 | Gualtier | 128/765 |
| 4,807,625 | 2/1989 | Singleton | 604/55 |

*Primary Examiner*—Max Hindenburg

[57] ABSTRACT

A method for using a syringe to remove an amniotic fluid specimen from a pregnant patient preparatory to the laboratory analysis is set forth. The method includes the steps of inserting an end of a syringe into the amniotic fluid source, withdrawing the fluid into the syringe, and filtering the fluid within the syringe.

1 Claim, 1 Drawing Sheet

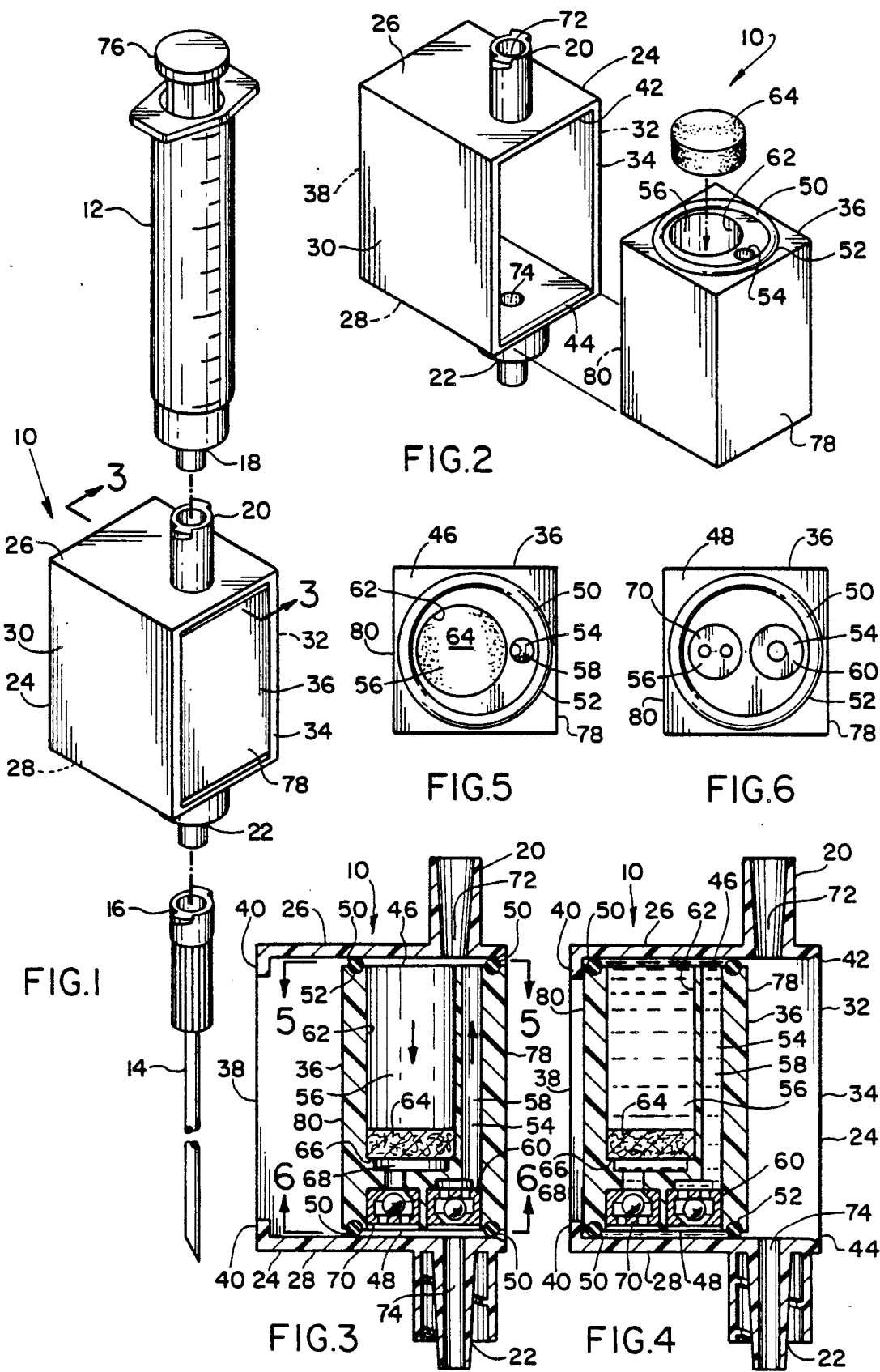

PRENATAL SPECIMEN COLLECTION METHOD

The present invention relates generally to improvements in collecting fluid specimens from a patient using a syringe, and more particularly to enhancing the collected specimen for subsequent laboratory analysis.

The within inventive method is particularly useful for amniocentesis, although it is not confined thereto and can be used, for example, also where cytologic examination of the collected specimen is contemplated, all as will be explained in greater detail subsequently herein.

BACKGROUND OF THE INVENTION

Amniocentesis is performed in pregnant women to determine genetic abnormalities prior to birth. It is used on women over 35 years of age, or with a family history of genetic disorders, chromosomal defects, mental retardation or RH incompatibility. Generally it is performed by placing a long 22 gauge needle into the uterus and withdrawing about 20 ml of amniotic fluid to be sent to the lab for analysis. This is usually performed between the 14th and 24th week of gestation. In addition to obtaining genetic information, the amniotic fluid also can be tested biochemically for Neural Tub Defects (alpha-fetoprotein), RH factor complications, creatine concentration, absence of bilirubin among others. The major problem with amniocentesis is that it can be performed only after the 14th week, and preferably not prior to the 16th week, and it can take from ten days to four weeks to cultivate a readable specimen. An abnormality such as Down's Syndrome (trisomy 21) may be the outcome of this test and most patients have an awesome dilemma whether to repeat the test (remote chance of error) or abort the fetus at that time. Repeating the test may result inconfirmation coming too late to safely abort the fetus. The only other technique for determining genetic information is called chorionic villus sampling (CVS) and can be done in the 8-10th week of gestation. DVS is still experimental and currently has a higher spontaneous abortion rate than ultrasound guided amniocentesis.

SUMMARY OF THE INVENTION

The amniotic fluid contains both material and embryonal derived cells thrown off by the fetus which can be collected and cultured to determine the genetic structure. The objective is to be able to make this determination earlier in the pregnancy to permit a confirming diagnosis, to treat the fetus in utero, or if necessary, to terminate a non-viable fetus. One of the problems of performing amniocentesis prior to the 16th week of pregnancy is that there is not a large volume of amniotic fluid available to withdraw. The within inventive method contemplates removing the amniotic fluid into a syringe, then returning the fluid back to the womb, filtering the fluid first to remove the fetal cells. The amniotic fluid is selectively recycled several times which results in the collection of a significantly larger number of cells than would have been present in a single withdrawal of a like amount of amniotic fluid.

Because of the concentration which results from the recycling, the within inventive method permits the early detection of fetal abnormalities perhaps as early as the 8th to 10th week. Although there is not much amniotic fluid at that stage, the recycling has been found to require only 2-3 cc of fluid and is still able to collect sufficient cells for subsequent laboratory analysis.

The inventive method hereof may also be expanded to include the collection and concentration of other body fluids where detection and characterization of cellular components, either human or microbiological, may improve diagnosis. For example, cytologic examination of cerebrospinal fluid, collected and concentrated by this invention, may be of diagnostic help in cases of suspected neoplasm-particularly meningeal leukemia or lymphoma, meningeal carcinoma of medulloblastoma. Cerebrospinal fluid, thus collected, may also be used in the diagnosis of CNS syphilis, fungal and bacterial (tuberculosis) meningitis and herpes simplex encephalitis.

BRIEF DESCRIPTION OF THE DRAWINGS

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective view of apparatus for practicing the within inventive method, namely a combination specimen collector and recycling syringe in disassembled relation;

FIG. 2 is similarly a perspective view, but of the components of the specimen collector in their unassembled condition;

FIG. 3 is a side elevational view, in section taken along line 3—3 of FIG. 1;

FIG. 4 is a sectional side elevational view similar to FIG. 3 but showing the specimen collector components in their non-recycling operational mode;

FIG. 5 is a plan view in section taken along line 5—5 of FIG. 3, and;

FIG. 6 is a bottom view in section taken along line 6—6 of FIG. 3.

In FIG. 1 a combination structure consisting of a specimen collector, generally designated 10, and the two components of a recycling syringe 12 and 14 for practicing the within inventive method is shown, the two components of the syringe 12 and 14 being illustrated in spaced relation above and below the collector 10. In practice, the proximal end 16 of the syringe needle 14 attaches to the bottom end 18 of the syringe plunger 12 by a coupling known as a "lure lock". The collection device 10 is designed to have a top attachable fitting 20 which is connectable to syringe end 18 and a bottom attachable fitting 22 that is connectable to end 16 of needle 14, so that all three components 10, 12 and 14 can be fastened together in vertical alignment.

As best seen in FIG. 2, the specimen collector 10 has an exterior boxlike housing member 24, to which the referred to fitting 20 is attached to the top wall 26 thereof and fitting 22 is part of the bottom wall 28. Housing member 24 also has respective front and back walls 30 and 32 which with top and bottom walls 26 and 28 bound a side opening 34 to receive therein a blocklike component 36. The interior corner 42 of top wall 26 and the interior corner 44 of bottom wall 28 are chamfered slightly, as best seen in FIG. 4. The left side 38 of member 24 is also open except for a pair of stop members 40, as best seen in FIGS. 3 and 4, for a purpose soon to be described.

Block 36 is of a square shape and size to fit freely within the cavity or compartment of box member 24, an operational mode depicted in FIG. 3. The top face 46 and bottom face 48 of block 36 are fitted with a pair of O-rings 50 that are seated in appropriate grooves 52. When O-rings 50 are in place and block 36 is within box member 24, a fluid tight interference fit takes place between block 36 and the top and bottom walls 26 and 28.

Since device 10 is intended to filter fluids initially drawn into syringe 12 and then discharged therefrom, block 36 has an "in" conduit 54 and an "out" conduit 56. "In" conduit 54 consists of a bore 58 whose upper end opens within the circumferential fluid seal of upper O-ring 50 to form a continuous fluid communication path to syringe 12 during the suction stroke of the syringe plunger 76. The lower end of conduit 54 is preferably fitted with a ball check valve 60 optionally with a similar flow check device, which allows for fluid flow from needle 14 only in the direction of the upwardly pointed arrow and thus towards syringe 12. Also positioned within the "seal" of upper O-ring 50 is the "out" conduit 56 which, it will be noted has a comparatively larger bore 62, so as to contribute to the retention of a fluid sample within the compartment provided by the bore 62. At the lower end of bore 62, a snug fitting filter element 64 is adapted in practice to be seated upon a shoulder 66 to provide the FIG. 5 position. Shoulder 66 locates the filter 64 in the flow path to an outflow chamber 68 which is provided under filter 64, said chamber 68 having an outlet controlled by check valve 70. Valve 70 is oriented or operatively arranged, in a well understood manner to allow one direction flow only away from syringe 12 and thus back to needle 14. Valves 60 and 70 will only be understood to have apertures within the "seal" areas of lower O-ring 50. In FIG. 3 it is to be noted that the "seal" area within upper O-ring 50 is part of the flow passage that is continuous with and thus is in fluid communication with opening 72. Likewise the "seal" area within lower O-ring 50 is part of the flow passage that is continuous with and in fluid communication with opening 74.

Collector 10 can be supplied assembled as shown in FIG. 1 or unassembled as shown in FIG. 2, but in either condition in a sanitized package, preparatory to being coupled and used with a standard syringe 12 and needle 14.

After assembly of the collection 10, if such assembly is needed, needle 14 is inserted within the fluid source (not shown), which will be understood to be in a contemplated circumstance amniotic fluid of a pregnant female patient, and plunger 76 is gently withdrawn creating a vacuum inside syringe 12. The amniotic or other body fluid is then drawn through needle 14, opening 74, check valve 60, bore 58, opening 72 and into syringe 12. During this fluid-withdrawal stroke it is to be noted that check valve 70 will be closed enabling a suction buildup which results in this directional flow.

When plunger 76 is reversed to apply pressure to the fluid in syringe 12 check valve 60 closes immediately and fluid from syringe 12 is forced through opening 72, bore 58, filter 64, chamber 68, check valve 70, opening 74 and ultimately out of the needle 14, a flow path depicted in FIG. 3 by the downwardly directed arrow.

After a selected number of alternating suction and pressure strokes of the syringe plunger 76, it is contemplated that the user will apply slight pressure on face 78 of block 36 so that block 36 slides to the left relative to housing 24, as viewed in FIG. 4, until contacting stops 40. Fluid content within chamber 62 of block 36, and more particularly the solids thereof are accumulated on filter 64 preparatory to being analyzed in a laboratory or the like. To this end unit 10 is uncoupled for further processing from syringe 12 and needle 14 followed by slight pressure on face 80 of block 36 to remove it from housing 24.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. The method of using a syringe to remove an amniotic fluid specimen from a pregnant patient preparatory to the laboratory analysis thereof comprising the steps of inserting the distal end of a syringe having a first passage and a second passage for moving fluid through said syringe into the patient amniotic fluid source, withdrawing amniotic fluid from said patient amniotic fluid source through said syringe first passage, maintaining said inserted position of said syringe and said first and second passages thereof so as to continue providing fluid communication between said syringe and said patient amniotic fluid source, returning said amniotic fluid through said syringe second passage to said patient amniotic fluid source incident to the operation of said syringe, filtering said amniotic fluid during the aforesaid return thereof using a removable filter in said maintained second fluid communication passage, selectively repeating the syringe removal and return through said filter of said amniotic fluid, and removing for laboratory analysis said filter with any content of said amniotic fluid repeatedly filtered therethrough, whereby there is provided an adequate amniotic fluid specimen for said laboratory analysis even during an early gestation period of the patient's pregnancy.

* * * * *